(12) United States Patent
Mou et al.

(10) Patent No.: US 11,937,903 B2
(45) Date of Patent: Mar. 26, 2024

(54) BLOOD PRESSURE DEVICE

(71) Applicant: MICROJET TECHNOLOGY CO., LTD., Hsinchu (TW)

(72) Inventors: Hao-Jan Mou, Hsinchu (TW); Yung-Lung Han, Hsinchu (TW); Chi-Feng Huang, Hsinchu (TW); Chang-Yen Tsai, Hsinchu (TW); Wei-Ming Lee, Hsinchu (TW); Chun-Yi Kuo, Hsinchu (TW); Chin-Wen Hsieh, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 497 days.

(21) Appl. No.: 17/136,237

(22) Filed: Dec. 29, 2020

(65) Prior Publication Data
US 2021/0204823 A1 Jul. 8, 2021

(30) Foreign Application Priority Data
Jan. 7, 2020 (TW) .................................. 109100512

(51) Int. Cl.
*A61B 5/021* (2006.01)
*A61B 5/00* (2006.01)
(Continued)

(52) U.S. Cl.
CPC ...... *A61B 5/02125* (2013.01); *A61B 5/02233* (2013.01); *A61B 5/0235* (2013.01);
(Continued)

(58) Field of Classification Search
None
See application file for complete search history.

(56) References Cited

U.S. PATENT DOCUMENTS 9,611,843 B2 * 4/2017 Hsueh .................. F04B 43/046
2011/0066009 A1 * 3/2011 Moon .................... A61B 5/743
600/509
(Continued)

FOREIGN PATENT DOCUMENTS

CN      107072538 A      8/2017
CN      109745022 A      5/2019
(Continued)

*Primary Examiner* — Yi-Shan Yang
(74) *Attorney, Agent, or Firm* — McClure, Qualey & Rodack, LLP

(57) ABSTRACT

A blood pressure device includes a first blood pressure measuring device, a second blood pressure measuring device, and a controller. The first blood pressure measuring device is to be worn on a first position of a wrist so as to obtain a first blood pressure information of the first position. The second blood pressure measuring device is to be worn on a second position of the wrist so as to obtain a second blood pressure information of the second position. The controller is electrically coupled to the first blood pressure measuring device and the second blood pressure measuring device so as to adjust tightness between the expanders and the user's skin, respectively. The controller receives, processes, and calculates a pulse transit time between the first blood pressure information and the second blood pressure information, and the controller obtains at least one blood pressure value based on the pulse transit time.

11 Claims, 19 Drawing Sheets

(51) Int. Cl.
*A61B 5/022* (2006.01)
*A61B 5/0235* (2006.01)
*A61B 5/024* (2006.01)

(52) U.S. Cl.
CPC .......... *A61B 5/681* (2013.01); *A61B 5/02416* (2013.01); *A61B 2562/0247* (2013.01)

(56) References Cited

U.S. PATENT DOCUMENTS

| | | | | |
|---|---|---|---|---|
| 2015/0359437 | A1* | 12/2015 | Maltz | A61B 5/6828 600/481 |
| 2018/0325395 | A1* | 11/2018 | Chen | F04B 39/10 |
| 2019/0001131 | A1* | 1/2019 | Ziv | A61N 1/36031 |
| 2019/0313924 | A1* | 10/2019 | Matsumura | A61B 5/02116 |
| 2020/0330037 | A1* | 10/2020 | Al-Ali | F04B 53/001 |
| 2021/0321953 | A1* | 10/2021 | Panneer Selvam | A61B 5/681 |

FOREIGN PATENT DOCUMENTS

| | | |
|---|---|---|
| CN | 109745023 A | 5/2019 |
| CN | 209018719 U | 6/2019 |
| TW | M547951 U | 9/2017 |
| TW | M576726 U | 4/2019 |
| TW | M582825 U | 9/2019 |

\* cited by examiner

BLOOD PRESSURE DEVICE

CROSS-REFERENCE TO RELATED APPLICATION

This non-provisional application claims priority under 35 U.S.C. § 119(a) to Patent Application No. 109100512 in Taiwan, R.O.C. on Jan. 7, 2020, the entire contents of which are hereby incorporated by reference.

BACKGROUND

Technical Field

The present disclosure relates to a blood pressure device. In particular, to a blood pressure device for measuring the pressure in the cardiovascular system.

Related Art

In recent years, awareness of personal health care has gradually increased so that the need of regularly monitoring the self-health condition has been generated. However, since most of the instruments for examining the body health condition are stationary facility, and people have to go to a medical service station or a hospital to obtain their health examination information. Even if there are already some detection devices for household uses on the market, sizes of these devices are still too large to be carried easily. In the current efficiency-pursuing society, these detection devices are hard to satisfy the needs of users.

Among the various health related indexes, the most representative one should be the blood pressure. The blood vessels in one's body are like roads spreading all over the body. Thus, the blood pressure is just like the road conditions, and the condition of the blood delivery can be understood through the blood pressure. If anything happens to the body, the blood pressure will reflect it clearly.

In view of these, how to provide a device, capable of accurately measuring the blood pressure of a user, combined with a wearable electronic device or a portable electronic device so that the user can quickly check the blood pressure whenever and wherever with the device is an issue raised currently.

SUMMARY

In general, one of the objects of present disclosure is to provide a blood pressure device for measuring the pressure in the cardiovascular system of a user. The blood pressure device is a wearable device, so that the user can carry the wearable device conveniently.

To achieve the above mentioned purpose(s), a general embodiment of the present disclosure provides a blood pressure device for measuring the blood pressure of the cardiovascular system of a user, the blood pressure device includes a first blood pressure measuring device, a second blood pressure measuring device, and a controller. The first blood pressure measuring device has a first expander and a first sensor. The first expander is capable of being worn on a first position of a wrist of the user and close-fitting the skin of the user in a non-invasive way, so that the first sensor close-fits against the skin of the user to obtain a first blood pressure information of the first position. The second blood pressure measuring device has a second expander and a second sensor. The second expander is capable of being worn on a second position of the wrist of the user and close-fitting the skin of the user in a non-invasive way, so that the second sensor close-fits against the skin of the user to obtain a second blood pressure information of the second position. The controller is electrically coupled to the first blood pressure measuring device and the second blood pressure measuring device so as to control the first expander to adjust tightness between the first expander and the skin of the user and to control the second expander to adjust tightness between the second expander and the skin of the user. The controller obtains a pulse transit time from the first blood pressure information and the second blood pressure information, and the controller generates at least one blood pressure value based on the pulse transit time.

BRIEF DESCRIPTION OF THE DRAWINGS

The disclosure will become more fully understood from the detailed description given herein below for illustration only, and thus not limitative of the disclosure, wherein.

DETAILED DESCRIPTION

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Figure 1A:
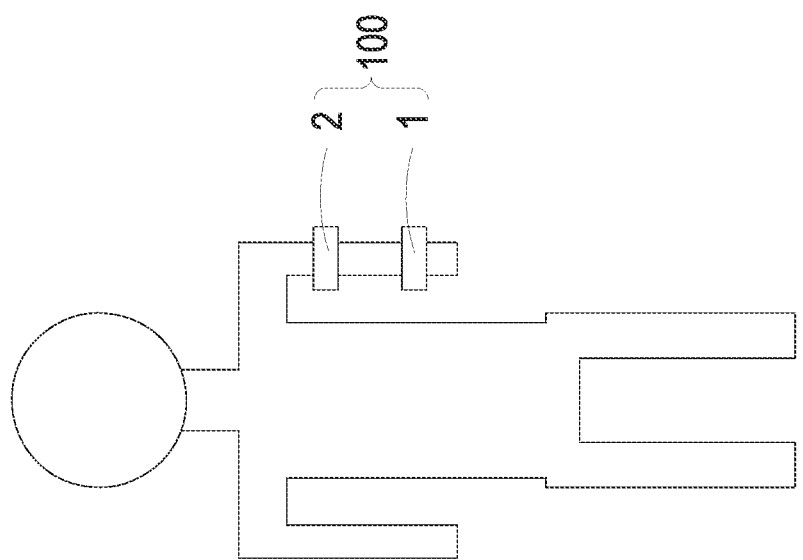
FIG. 1A illustrates a schematic view of a configuration of a blood pressure device according to an exemplary embodiment of the present disclosure.
Figure 1B:
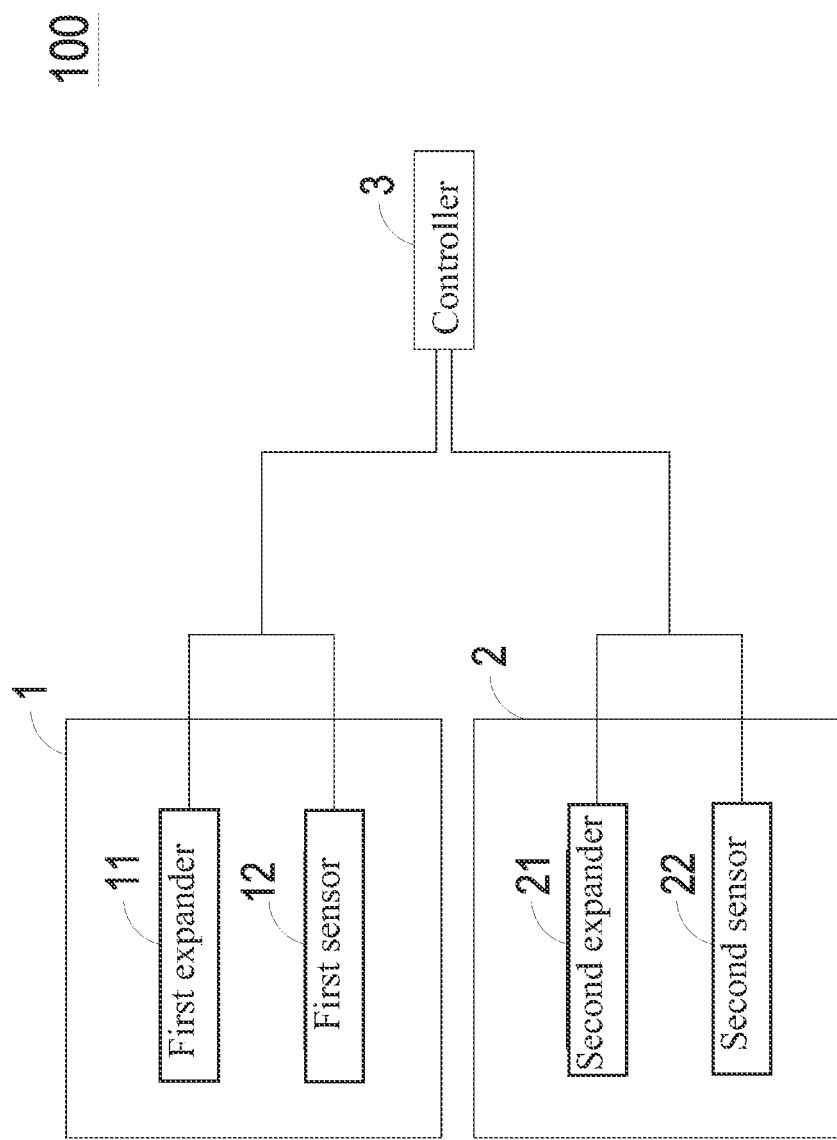
FIG. 1B illustrates a schematic block diagram of the blood pressure device according to the exemplary embodiment of the present disclosure.

Please refer to FIG. 1A and FIG. 1B. The present disclosure provides a blood pressure device 100 for measuring the blood pressure of the cardiovascular system of a user. The blood pressure device 100 is applied to the radial artery at the user's wrist and close-fits the skin of the user's wrist in a non-invasive way. The blood pressure device 100 includes a first blood pressure measuring device 1, a second blood pressure measuring device 2, and a controller 3.

Figure 2:
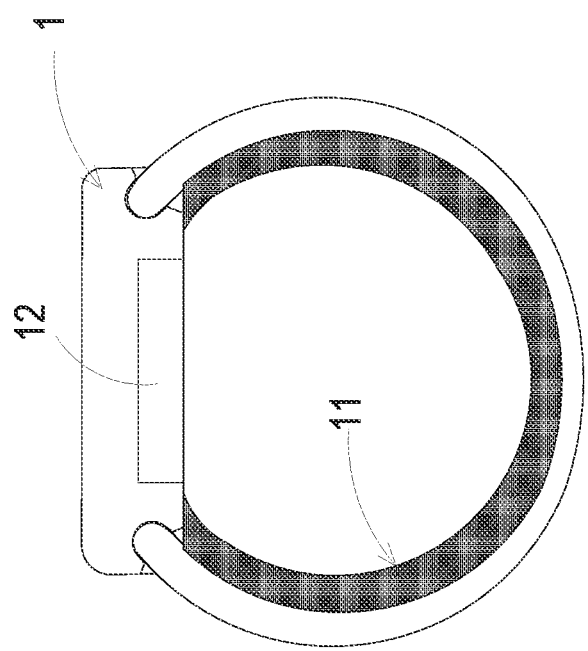
FIG. 2 illustrates a schematic view of a first blood pressure measuring device according to the exemplary embodiment of the present disclosure.

Please refer to FIG. 1B and FIG. 2. The first blood pressure measuring device 1 has a first expander 11 and a first sensor 12. The first expander 11 can be worn on a first position of the use's wrist and close-fits the skin of the user in a non-invasive way. In this embodiment, the first position is above the radial artery of the user's wrist, but is not limited thereto. The first blood pressure measuring device 1 is located on the radial artery of the user's wrist (i.e. the first position) so that the first sensor 12 can close-fit against the skin of the user. When a pulse of blood pressure (also referred to "blood pressure pulse") arrives the first position of the user's wrist, the first sensor 12 can measure a first blood pressure information of the first position.

Figure 3:
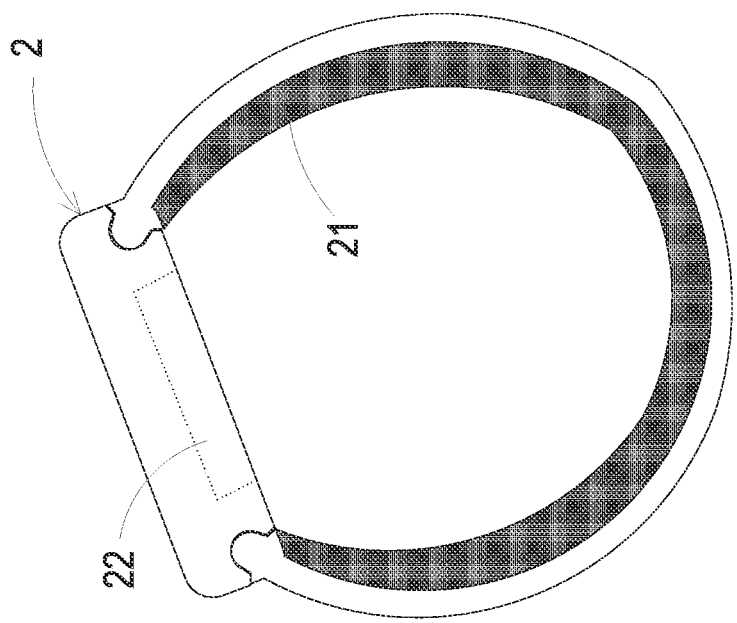
FIG. 3 illustrates a schematic view of a second blood pressure measuring device according to the exemplary embodiment of the present disclosure.

Please refer to FIG. 1B and FIG. 3. The second blood pressure measuring device 2 has a second expander 21 and a second sensor 22. The second expander 21 can be worn on a second position of the use's wrist and close-fits the skin of the user in a non-invasive way. In this embodiment, the second position deviates from the user's wrist. That is, the second position is away from the user's wrist joint, but is not limited thereto. Thus, even the second blood pressure measuring device 2 is worn on the second positon, the user still can bend or straighten his/her joint without being restricted. The second blood pressure measuring device 2 is located on the second position of the user's wrist so that the second sensor 22 can close-fit against the skin of the user. When the pulse of blood pressure arrives the second position of the user's wrist, the second sensor 22 can measure a second blood pressure information of the second position.

Please refer to FIG. 1B. The controller 3 is electrically coupled to the first expander 11 and the first sensor 12 of the first blood pressure measuring device 1 as well as the second expander 21 and the second sensor 22 of the second blood pressure measuring device 2. The controller 3 controls the first expander 11 and the second expander 21 so as to adjust the first expander 11 and the second expander 21 to be capable of being worn on the user, and the controller 3 controls the tightness between each of the expanders and the skin of the user. That is, the controller 3 controls the first expander 11 to adjust the tightness between the first expander 11 and the skin of the user; and the controller 3 controls the second expander 21 to adjust the tightness between the second expander 21 and the skin of the user. The controller 3 receives and processes the first blood pressure information obtained by the first sensor 12 and the second blood pressure information obtained by the second sensor 22. The first blood pressure information and the second blood pressure information respectively have the time information when the pulse of the blood pressure arrives the first position (the first sensor 12) of the user's wrist and the time information when the pulse of the blood pressure arrives the second position (the second sensor 22) of the user's wrist. Then, the controller 3 calculates the pulse transit time (PTT) of the pulse of the blood pressure between the second position (the second sensor 22) and the first position (the first sensor 12). Accordingly, the controller 3 can generate one or more blood pressure values of the user based on the pulse transit time so as to retrieve a blood pressure information of the user. Moreover, the first sensor 12 and the second sensor 22 respectively can be a photo-plethysmographic (PPG) sensor or a pulse pressure sensor.

The first sensor 12 may be a pulse pressure sensor. The pulse pressure sensor may include at least one pressure sensor (not shown) located on the radial artery of the user's wrist (the first position) and optionally may include an accelerometer (not shown) or a strainmeter (not shown). The pressure sensor can detect when the pulse of the blood pressure arrives the position of the pressure sensor. The accelerometer and/or the strainmeter are/is used to detect the current condition of the user. When the body condition of the user changes acutely, such as the user is hit by an external force or the user falls down suddenly, the accelerometer and/or the strainmeter drive(s) the controller 3 to confirm the blood pressure information of the user so as to determine whether the user needs help/emergency aid or not.

Figure 4:
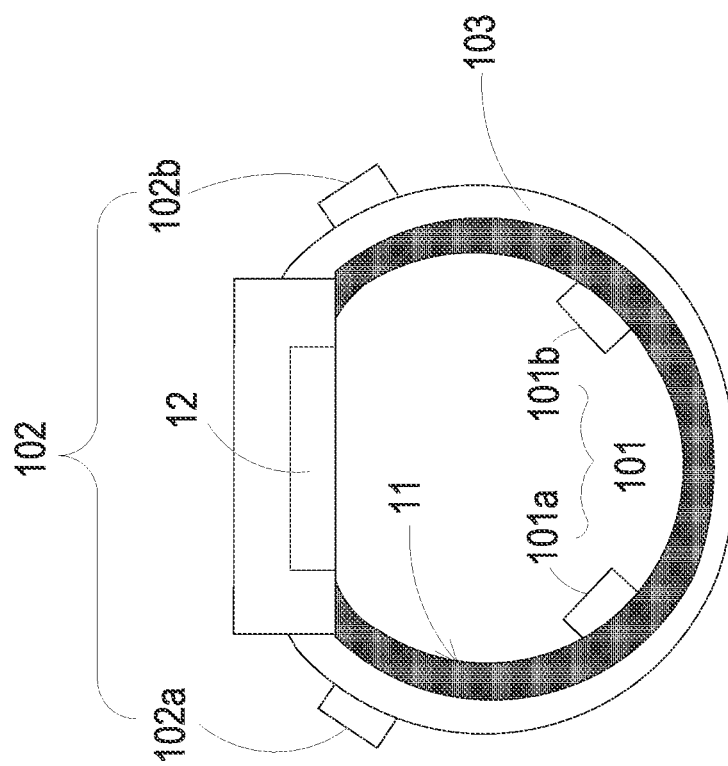
FIG. 4 illustrates a schematic view of a wrist wearable device according to an exemplary embodiment of the present disclosure.

In some embodiments, the blood pressure device 100 may be a wrist wearable device. As shown in FIG. 4, the wrist wearable device may include an elongated wrist band 103 suitable for being worn on a wrist. A first electrode pair 101 and a second electrode pair 102 are respectively disposed on the wrist band 103. When the wrist wearable device is worn on the user's wrist, the first electrode pair 101 close-fits against the user's skin in a non-invasive manner. The first electrode pair 101 includes a first current driving electrode 101a and a first sensor electrode 101b. The first current driving electrode 101a is configured to transmit a driving current between the user's wrist and the first current driving electrode 101a, and the first sensor electrode 101b is configured to measure a first voltage level of the user. The second electrode pair 102 is located on the outer side of the wrist wearable device, so that the second electrode pair 102 can be interacted with the user more conveniently. The second electrode pair 102 includes a second current driving electrode 102a and a second sensor electrode 102b. The second current driving electrode 102a is configured to transmit a driving current between the user's wrist and the second current driving electrode 102a, and the second sensor electrode 102b is configured to measure a second voltage level of the user. The first expander 11 and the first sensor 12 of the first blood pressure measuring device 1 are disposed on a surface of the wrist wearable device. Moreover, the first sensor 12 is coupled to the wrist wearable device so as to detect when the pulse of the blood pressure arrives the first position of the user's wrist. The controller 3 is also configured to process the detected signal of the first voltage level and that of the second voltage level, by which the controller 3 can detect when the blood is pumped out from the left ventricle of the user's heart to obtain the second blood pressure information. Further, the controller 3 obtains the first blood pressure information according to the data showing when the blood pressure pulse corresponding to the pumped blood arrives the first position of the user's wrist. The controller 3 further obtains the pulse transit time (PTT) of the blood pressure pulse by calculating a time difference between the blood being pumped out from the left ventricle (ventricular ejection time) and being transmitted to the first position (the first sensor 12) based on the first blood pressure information and the second blood pressure information. Then, the controller 3 obtains one more blood pressure value of the user based on the pulse transit time.

Figure 5:
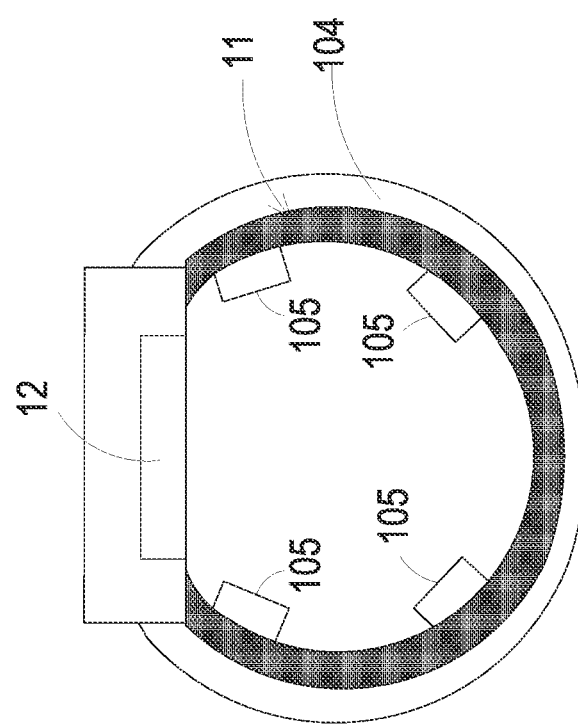
FIG. 5 illustrates a schematic view of a wrist wearable device according to another exemplary embodiment of the present disclosure.

Please refer to FIG. 5. FIG. 5 schematically represents another embodiment of a wrist wearable device for measuring blood pressure. In this embodiment, the wrist wearable device includes an elongated band 104 and at least four third electrodes 105. The third electrode 105 may be, but not limited to, an Electrocardiography (ECG/EKG) electrode or an impedance cardiogram (ICG) electrode. The elongated band 104 extends around the user's wrist and close-fits the user's skin in a non-invasive way. The third electrodes 105 are coupled to the elongated band 104 for detecting the ventricular ejection time of the ventricle of the user's heart to obtain a second blood pressure information. The first expander 11 and the first sensor 12 of the first blood pressure measuring device 1 are disposed on the wrist wearable device and are coupled to the elongated band 104 for detecting when the blood pressure pulse corresponding to the second blood pressure information arrives the first position of the user's wrist, so that a first blood pressure information can be generated. The controller 3 obtains the pulse transit time of the blood pressure pulse by calculating a time difference between the ventricular ejection and the pulse arrival at the wrist based on the first blood pressure information and the second blood pressure information. The controller 3 obtains one or more relative blood pressure values of the user based on the pulse transit time. In one embodiment, the first sensor 12 is preferably a photoplethysmography sensor, but is not limited thereto.

Figure 6A:
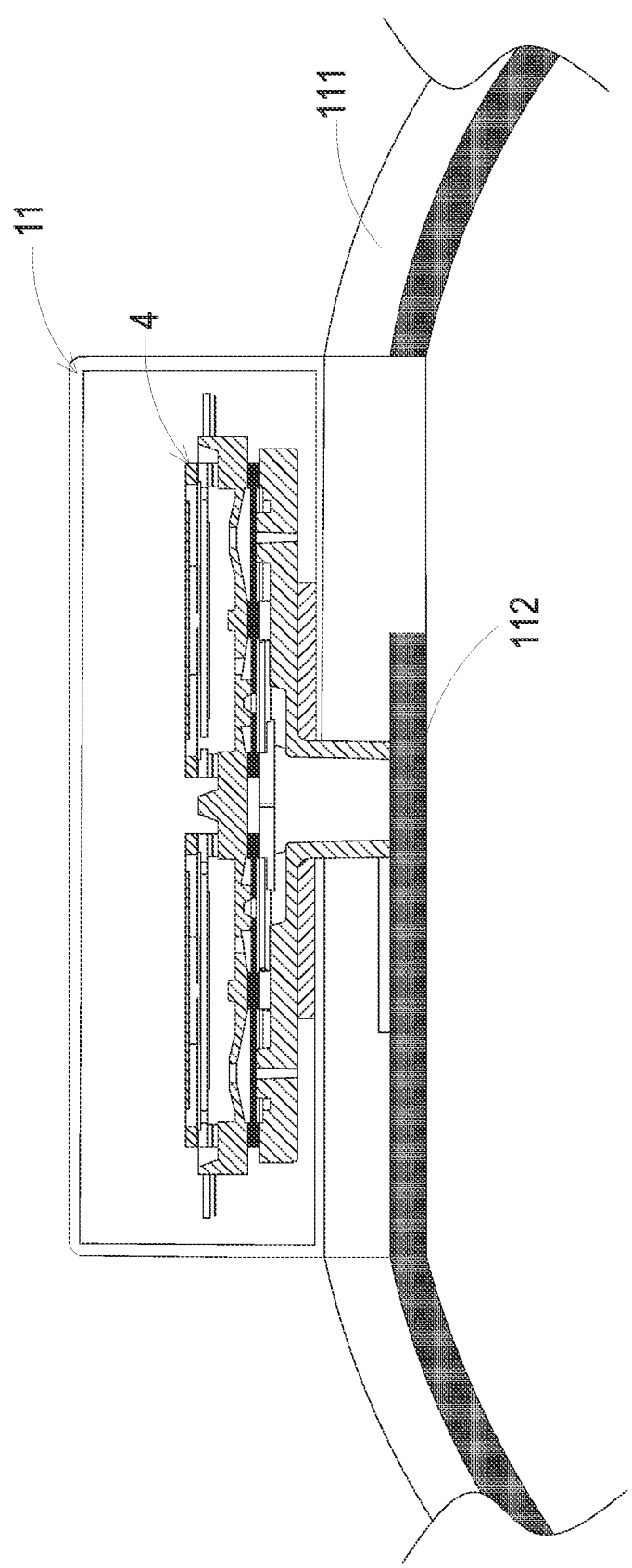
FIG. 6A and FIG. 6B illustrate schematic views of a wrist wearable device according to still another exemplary embodiment of the present disclosure.
Figure 6B:
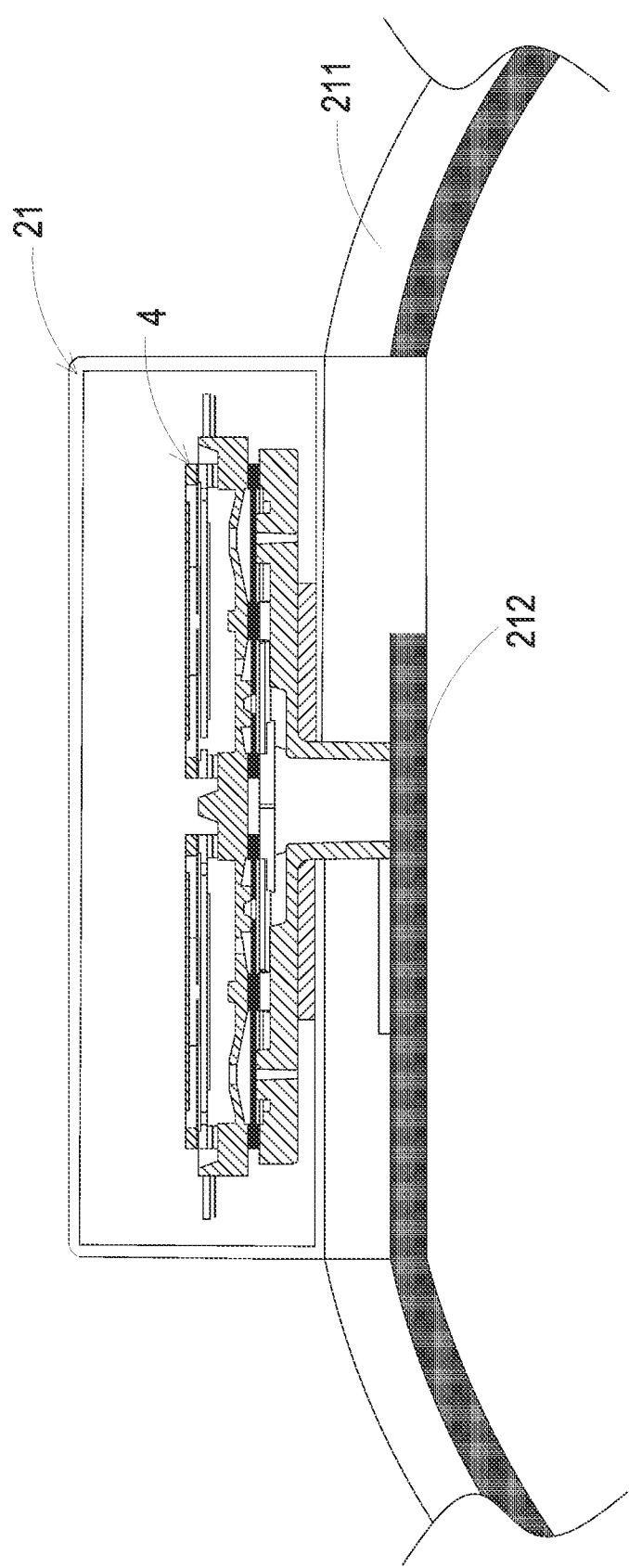

Please refer to FIG. 6A and FIG. 6B. The first expander 11 and the second expander 21 respectively have an actuator 4, and both the first expander 11 and the second expander 21 are controlled to be inflated and expanded by their corresponding actuators 4. In this embodiment, the first expander 11 and the second expander 21 are respectively a first annular belt structure 111 made of elastic material and a second annular belt structure 211 made of elastic material so as to wrap around the user's arm, wrist, or the like. The first expander 11 may have a first gas bag 112 and the second expander 21 may have a second gas bag 212, respectively. The first gas bag 112 is disposed at the inner side of the first annular belt structure 111 and shrinks to form a flat surface. The second gas bag 212 is disposed at the inner side of the second annular belt structure 211 and shrinks to form a flat surface. The first gas bag 112 and the second gas bag 212 are controlled by their corresponding actuators 4 to be inflated and expanded.

Please refer to FIG. 7A to FIG. 7G. The actuator 4 includes a valve device 5 and a gas transmission device 6. The gas transmission device 6 is disposed on one side of the valve device 5 and covers the one side of the valve device 5, such that the gas transmission device 6 and the valve device 5 are assembled as one component. The valve device 5 includes a convergence plate 51, at least one chamber plate 52, and at least one valve sheet 53. Please refer to FIG. 7B and FIG. 7C. The convergence plate 51 has a convergence plate first surface 51a and a convergence plate second surface 51b, which are opposite to each other. A plurality of convergence plate assembly areas 51c can be defined on the convergence plate 51. The number of the convergence plate assembly areas 51c may be adjusted depending on the number of the component set (including one chamber plate 52, one valve plate 53, and one gas transmission device 6) desired to be assembled on the convergence plate 51. A convergence outlet 511 is disposed on the convergence plate 51 and penetrates the convergence plate 51 from the convergence plate first surface 51a to the convergence plate second surface 51b. Each of the convergence plate assembly areas 51c has a convergence trough 513, a convergence plate convex portion 514, a discharge trough 515, and a discharge outlet 516. The convergence trough 513, the convergence plate convex portion 514, and the discharge trough 515 are disposed on the convergence plate second surface 51b. A guiding channel 512 communicating with the convergence outlet 511 and the convergence trough 513 is disposed on the convergence plate second surface 51b and served as a connecting passage between the convergence trough 513 and the discharge trough 515. The convergence plate convex portion 514 protrudes from the discharge trough 515 and is surrounded by the discharge trough 515. The discharge outlet 516 is disposed at the central portion of the convergence plate convex portion 514, and the discharge outlet 516 penetrates the convergence plate 51 from the convergence plate first surface 51a to the convergence plate second surface 51b. Accordingly, as the convergence plate second surface 51b of the convergence plate 51 correspondingly covers the chamber plate 52, the gas discharged out by the chamber plate 52 can be converged at the guiding channel 512 of the convergence plate 51. Then, the gas can be guided to the convergence outlet 511 through the guiding channel 512 and be discharged out afterwards. Conversely, it should be noted that, in the embodiment that a plurality of convergence plate assembly areas 51c is defined on the convergence plate 51, only one convergence outlet 511 is disposed on the convergence plate 51 for converging gas, and a plurality of discharge outlets 516 are disposed on the convergence plate 51 for discharging gas.

Figure 7A:
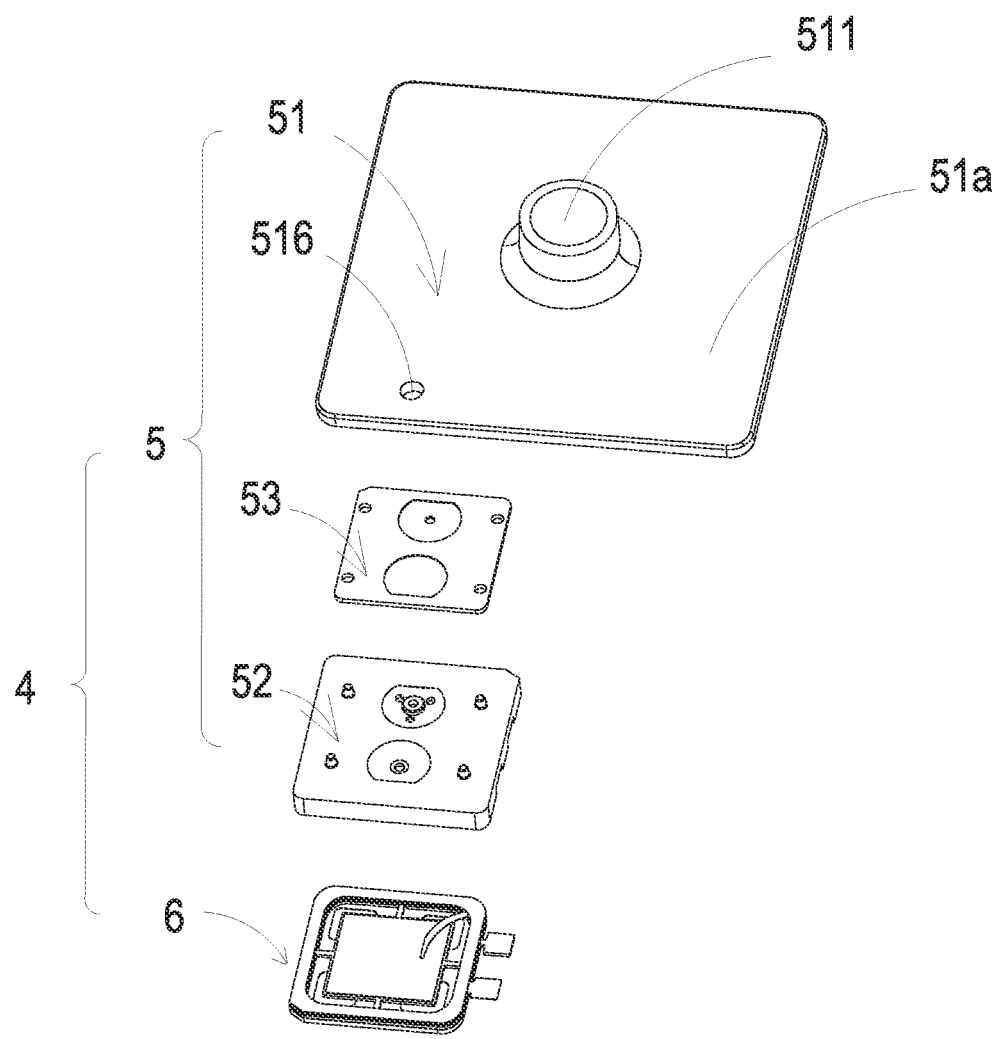
FIG. 7A illustrates a schematic exploded view of an actuator according to an exemplary embodiment of the present disclosure.
Figure 7B:
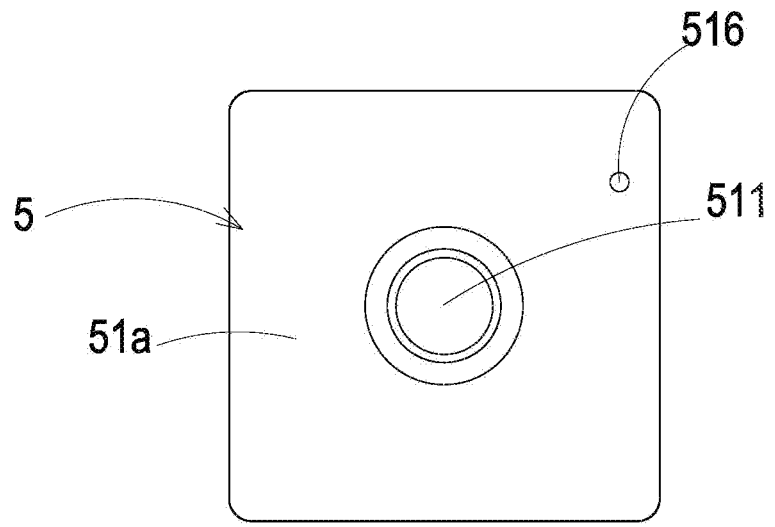
FIG. 7B illustrates a schematic top view of the convergence plate shown in FIG. 7A.
Figure 7C:
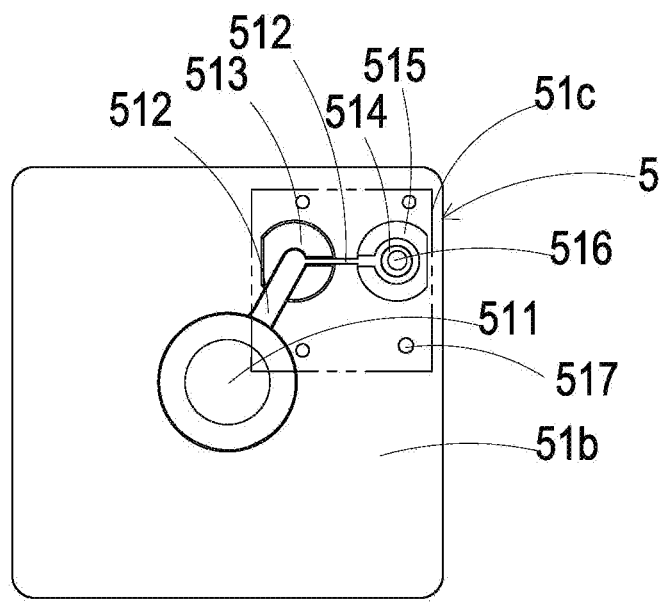
FIG. 7C illustrates a schematic bottom view of the convergence plate shown in FIG. 7A.
Figure 7D:
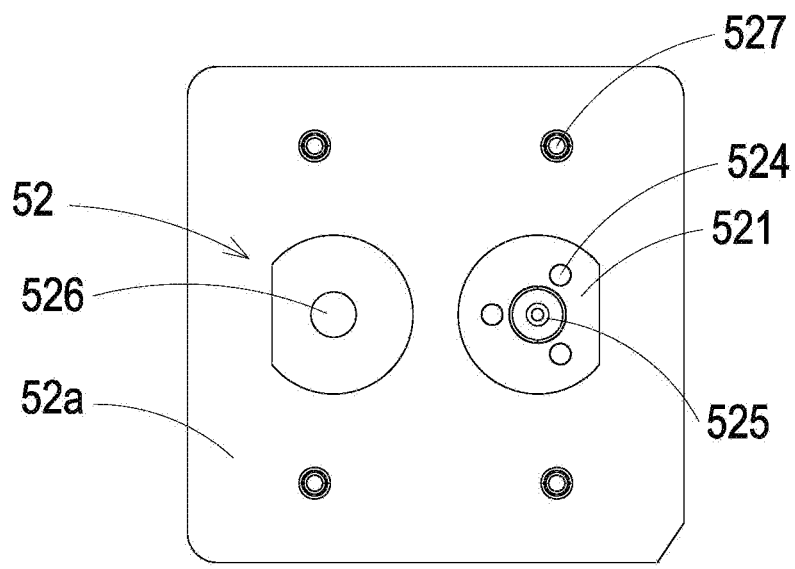
FIG. 7D illustrates a schematic top view of the chamber plate shown in FIG. 7A.
Figure 7E:
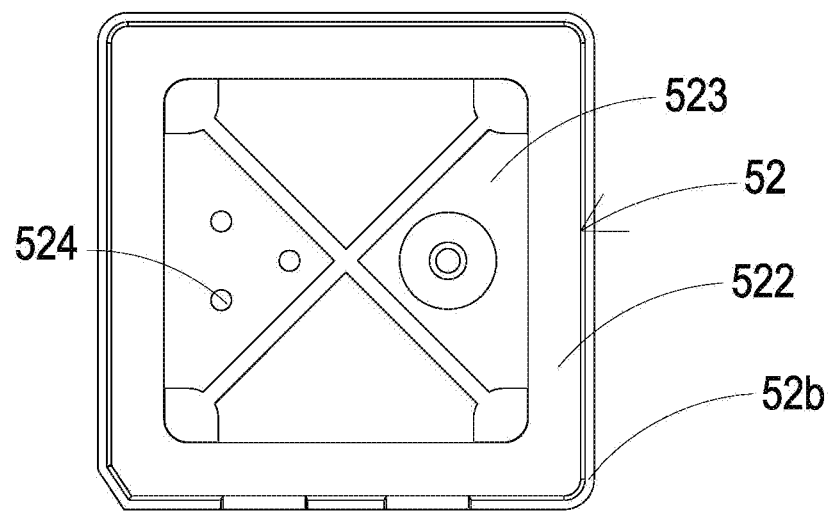
FIG. 7E illustrates a schematic bottom view of the chamber plate shown in FIG. 7A.

Please refer to FIG. 7D and FIG. 7E. The chamber plate 52 has a chamber plate first surface 52a and a chamber plate second surface 52b, which are opposite to each other. The convergence plate 51 is placed on the chamber plate first surface 52a. The chamber plate first surface 52a is recessed to form a flow guiding chamber 521. The chamber plate second surface 52b is recessed to form a receiving trough 522. The flow guiding chamber 521 corresponds to the convergence trough 513 of the convergence plate 51 and is in communication with the convergence trough 513. In other words, the flow guiding chamber 521 and the receiving trough 522 are respectively disposed on two opposite surfaces of the chamber plate 52. A confluence chamber 523 is disposed on a bottom of the receiving trough 522, and at least one communication hole 524 is disposed on a bottom of the confluence chamber 523. The communication hole 524 penetrates the chamber plate 52, so that the confluence chamber 523 can communicate with the flow guiding chamber 521. In this embodiment, the number of the communication holes 524 is three, but is not limited thereto. A chamber plate convex portion 525 is disposed in the flow guiding chamber 521, and the communication holes 524 are disposed around the chamber plate convex portion 525. A second communication hole 526 is disposed on a portion of the chamber plate 52 corresponding to the discharge trough 515 of the convergence plate 51. The second communication hole 526 penetrates the chamber plate first surface 52a of the chamber plate 52 and communicates with the confluence chamber 523.

Figure 7F:
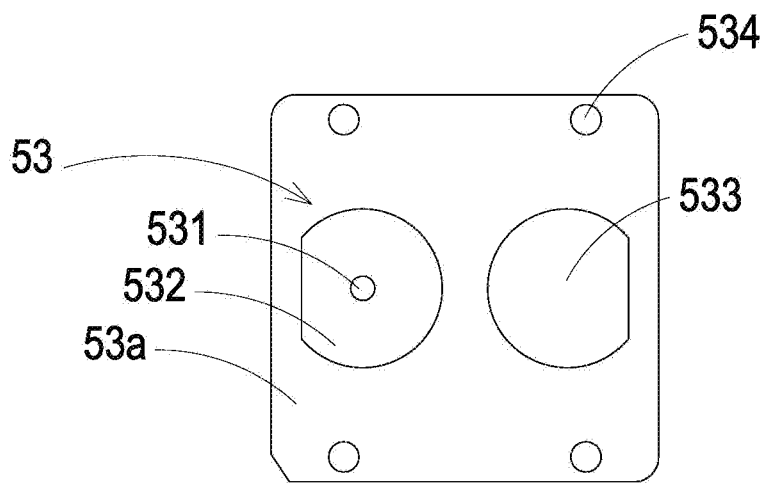
FIG. 7F illustrates a schematic top view of the valve sheet shown in FIG. 7A.
Figure 7G:
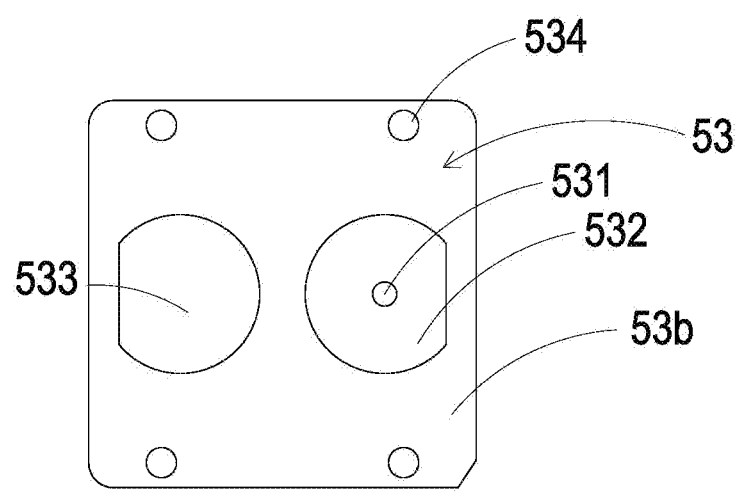
FIG. 7G illustrates a schematic bottom view of the valve sheet shown in FIG. 7A.
Figure 8A:
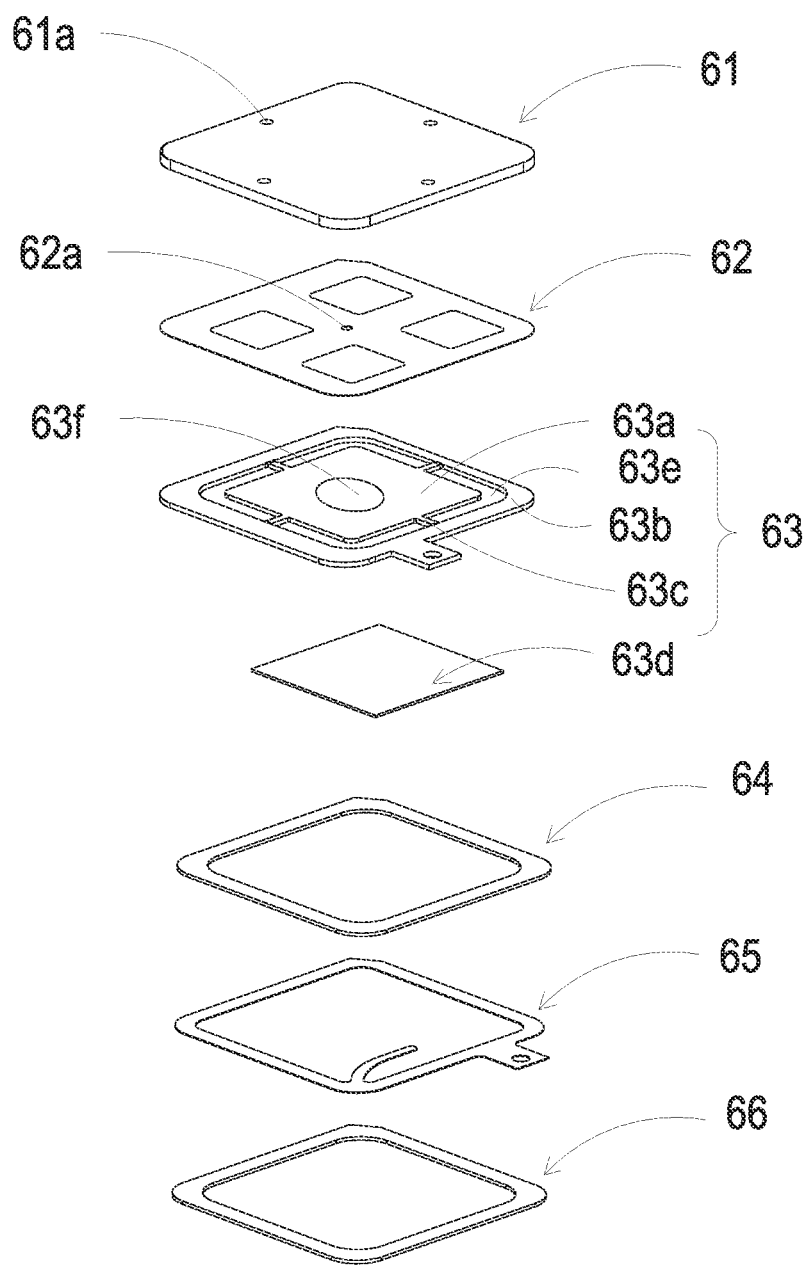
FIG. 8A illustrates a front exploded view of a micro pump according to an exemplary embodiment of the present disclosure.
Figure 8B:
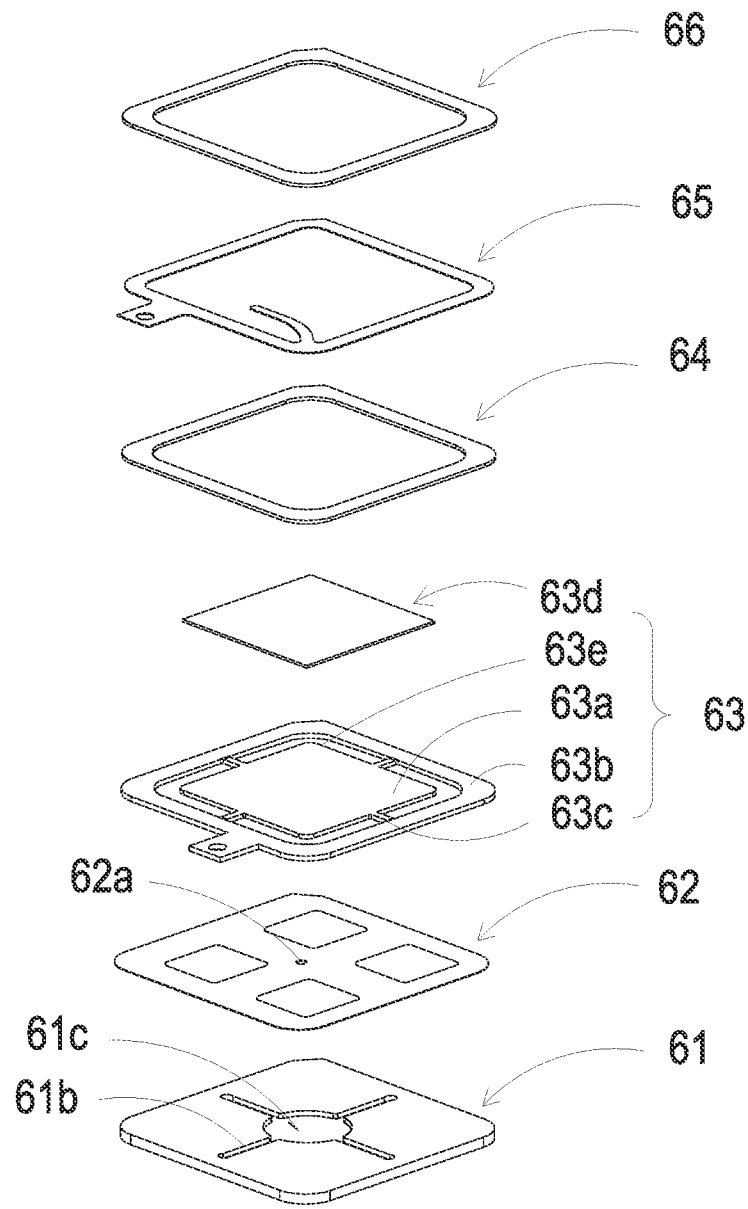
FIG. 8B illustrates a rear exploded view of the micro pump according to the exemplary embodiment of the present disclosure.

Please refer to FIG. 7F and FIG. 7G. The valve sheet 53 is disposed between the convergence plate 51 and the chamber plate 52. When the valve sheet 53 is disposed and positioned on the chamber plate first surface 52a of the chamber plate 52, the valve sheet 53 correspondingly abuts against the chamber plate convex portion 525 of the chamber plate 52. A valve hole 531 is disposed on the valve sheet 53 and corresponds to the chamber plate convex portion 525, and thus the valve hole 531 is closed by the chamber plate convex portion 525. Moreover, when the convergence plate 51 is disposed and positioned on the valve sheet 53, the valve sheet 53 correspondingly abuts against the convergence plate convex portion 514 of each of the convergence plate assembly areas 51c. Moreover, in this embodiment, the valve sheet 53 may have a first contact surface 53a and a second contact surface 53b. A convergence concave sheet 532 and a discharge concave sheet 533 are disposed between the first contact surface 53a and the second contact surface 53b, and the convergence concave sheet 532 and the discharge concave sheet 533 do not protrude out of the first contact surface 53a and the second contact surface 53b. The convergence concave sheet 532 correspondingly abuts against the chamber plate convex portion 525 of the chamber plate 52. The valve hole 531 is disposed at the convergence concave sheet 532 and thus is closed by the chamber plate convex portion 525. The discharge concave sheet 533 correspondingly abuts against the convergence plate convex portion 514 of each of the convergence plate assembly areas 51c of the convergence plate 51, and thus closes the discharge outlet 516.

In this embodiment, in order to stably fix the valve sheet 53 between the chamber plate 52 and the convergence plate 51 without being moved, a plurality of latches 527 is disposed on the chamber plate first surface 52a of the chamber plate 52. The valve sheet 53 is disposed on the chamber plate first surface 52a of the chamber plate 52, and the valve sheet 53 has positioning holes 534 corresponding to the latches 527. The convergence plate 51 is disposed on the valve sheet 53, and the convergence plate 51 has latch grooves 517 corresponding to the positioning holes 534. Therefore, when the valve sheet 53 is disposed between the chamber plate 52 and the convergence plate 51, each of the latches 527 of the chamber plate 52 can be firstly inserted into the corresponding positioning hole 534 of the valve sheet 53, and then can be inserted into the corresponding latch groove 517 of the convergence plate 51, so that the valve sheet 53 can be positioned without being moved.

Please further refer to FIG. 8A, FIG. 8B, and FIG. 9A to FIG. 9E. In some embodiments, the gas transmission device 6 mentioned above may be a micro pump to control the gas flow in the blood pressure device. The gas transmission device 6 is disposed in the receiving trough 522 of the chamber plate 52 so as to seal the confluence chamber 523 and to transmit the gas to the confluence chamber 523. The gas transmission device 6 is sequentially stacked by an inlet plate 61, a resonance sheet 62, a piezoelectric actuator 63, a first insulation sheet for plate) 64, a conductive sheet for plate) 65, and a second insulation sheet for plate) 66. The inlet plate 61 has at least one inlet hole 61a, at least one convergence channel 61b, and a convergence chamber 61c. The inlet hole 61a is configured to guide the gas to flow into the micro pump. The inlet hole 61a correspondingly penetrates the inlet plate 61 and is in communication with the convergence channel 61b, and the convergence channel 61b is in communication with the convergence chamber 61c, so that the gas guided by the inlet hole 61a can be converged at the convergence chamber 61c through the convergence channel 61b. In this embodiment, the number of the inlet holes 61a and the number of the convergence channels 61b are the same, and the number of the inlet holes 61a and the number of the convergence channels 61b may be both four, but is not limited thereto. The four inlet holes 61a are respectively in communication with the four convergence channels 61b, and the four convergence channels 61b are in communication with the convergence chamber 61c.

The resonance sheet 62 may be assembled with the inlet plate 61 through attaching, and the resonance sheet 62 has a perforation 62a, a movable portion 62b, and a fixed portion 62c. The perforation 62a is disposed at the center portion of the resonance sheet 62 and corresponds to the convergence chamber 61c of the inlet plate 61. The movable portion 62b is disposed at the periphery of the perforation 62a and corresponds to the convergence chamber 61c of the inlet plate 61. The fixed portion 62c is disposed at the periphery of the resonance sheet 62 and attached to the inlet plate 61.

The piezoelectric actuator 63 includes a suspension plate 63a, an outer frame 63b, at least one supporting element 63c, a piezoelectric element 63d, at least one gap 63e, and a protruding portion 63f. In some embodiments of the present disclosure, the suspension plate 63a is in square shape. It is understood that, the reason why the suspension plate 63a adopts the square shape is that, comparing with a circle suspension plate having a diameter equal to the side length of the square suspension plate 63a, the square suspension plate 63a has an advantage of saving electricity. The power consumption of a capacitive load operated at a resonance frequency may increase as the resonance frequency increases, and since the resonance frequency of a square suspension plate 63a is much lower than that of a circular suspension plate, the power consumption of the square suspension plate 63a is relatively low as well. Consequently, the square design of the suspension plate 63a used in one or some embodiments of the present disclosure has the benefit of power saving. The outer frame 63b is disposed around the periphery of the suspension plate 63a. The at least one supporting element 63c is connected between the suspension plate 63a and the outer frame 63b to provide a flexible support for the suspension plate 63a. The piezoelectric element 63d has a side length, and the side length of the piezoelectric element 63d is shorter than or equal to a side length of the suspension plate 63a. The piezoelectric element 63d is attached to a surface of the suspension plate 63a so as to drive the suspension plate 63a to bend and vibrate when the piezoelectric element 63d is applied with a voltage. The at least one gap 63e is formed between the suspension plate 63a, the outer frame 63b, and adjacent supporting elements 63c, and the at least one gap 63e is provided for the gas to flow therethrough. The protruding portion 63f is disposed on a surface of the suspension plate 63a opposite to the surface of the suspension plate 63a where the piezoelectric element 63d is attached. In this embodiment, the protruding portion 63f may be a protruding structure integrally formed with suspension plate 63a by a lithography process, and the protruding portion 63f is protruding from the surface of the suspension plate 63a opposite to the surface of the suspension plate 63a where the piezoelectric element 63d is attached.

Figure 9A:
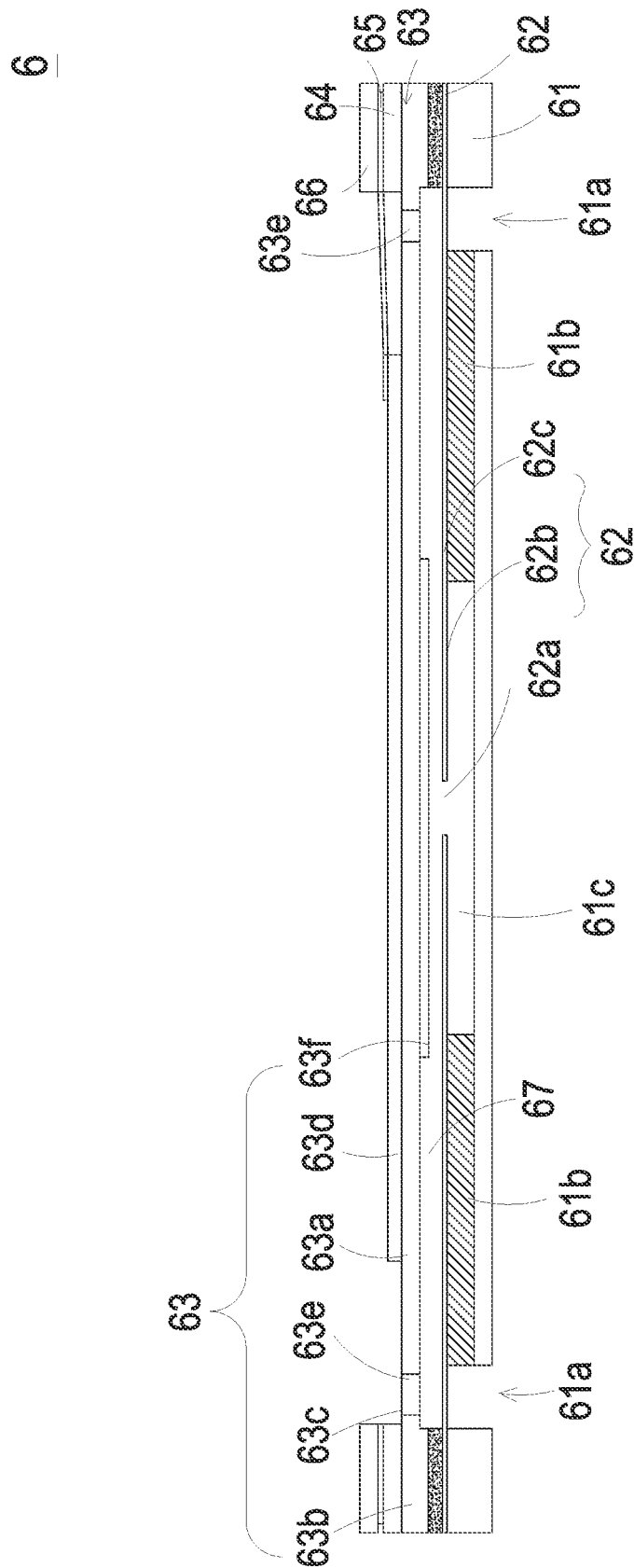
FIG. 9A illustrates a schematic cross-sectional view of the micro pump according to the exemplary embodiment of the present disclosure.
Figure 9B:
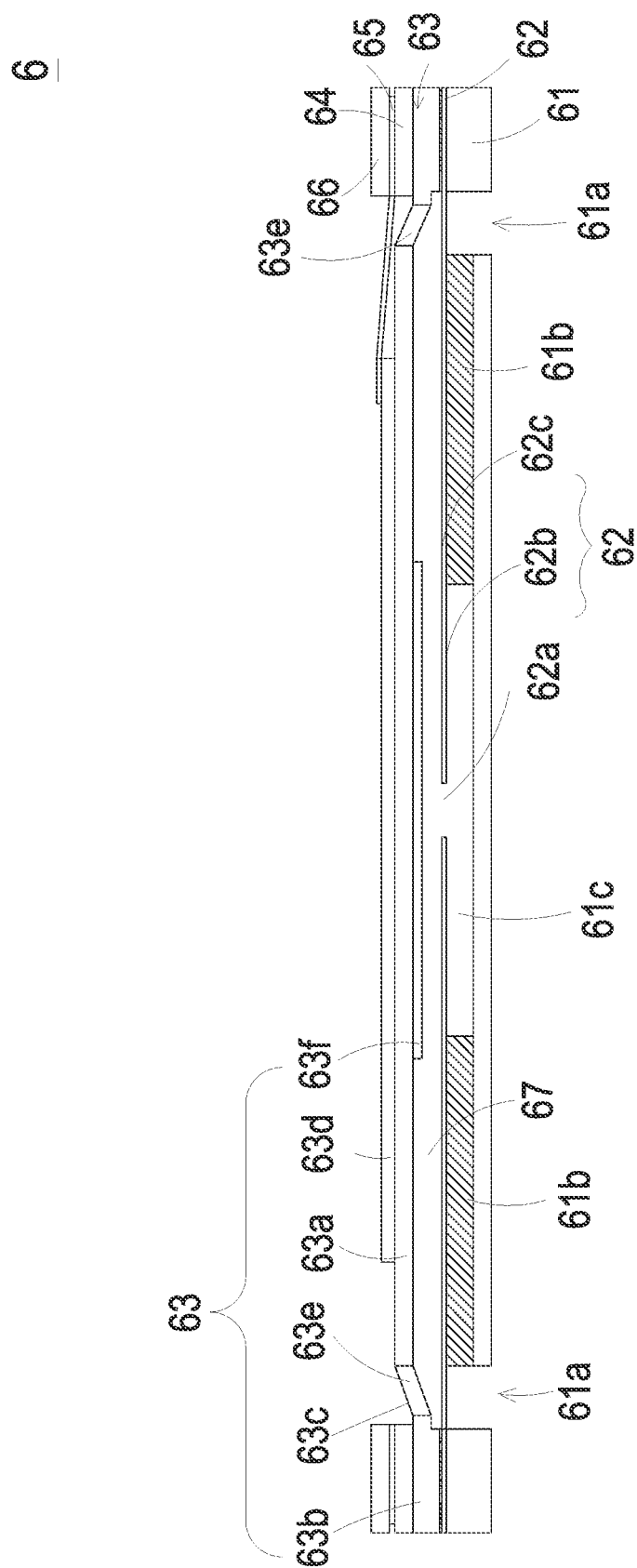
FIG. 9B illustrates a schematic cross-sectional view of the micro pump according to another exemplary embodiment of the present disclosure.

The inlet plate 61, the resonance sheet 62, the piezoelectric actuator 63, the first insulation plate 64, the conductive plate 65, and the second insulation plate 66 are sequentially stacked and assembled with each other. A chamber space 67 is formed between the suspension plate 63a and the resonance sheet 62. The chamber space 67 can be formed by filling a material, such as conductive adhesive, between the resonance sheet 62 and the outer frame 63b of the piezoelectric actuator 63, but not limited thereto. By filling a material between the resonance sheet 62 and the suspension plate 63a, a certain distance can be maintained between the resonance sheet 62 and the suspension plate 63a to form the chamber space 67, by which the gas can be guided to flow more quickly. Further, since an appropriate distance is maintained between the suspension plate 63*a* and the resonance sheet 62, the interference raised by the contact between the suspension plate 63*a* and the resonance sheet 62 can be reduced, so that the generation of noise can be decreased as well. In other embodiments, the required thickness of the conductive adhesive between the resonance sheet 62 and the outer frame 63*b* of the piezoelectric actuator 63 may be decreased by increasing the height of the outer frame 63*b* of the piezoelectric actuator 63, and the chamber space 67 still can be formed. Accordingly, during the assembling process of the gas transmission device 6, the entire structure of the gas transmission device 6 would not be indirectly affected under the hot pressing temperature and the cooling temperature owing to the filling material of the conductive adhesive selected, thereby avoiding the situation that the actual spacing of the resulted chamber space 67 being affected by the thermal expansion and contraction of the filling material of the conductive adhesive, but embodiments are not limited thereto. Moreover, the size of the chamber space 67 also affects the transmission efficiency of the gas transmission device 6. Therefore, it is important to maintain a fixed size of the chamber space 67 for the gas transmission device 6 to provide a stable transmission efficiency. Thus, as shown in FIG. 9B, in some other embodiments, the suspension plate 63*a* can be extended outwardly a certain distance by stamping. The extension distance can be adjusted by at least one supporting element 63*c* formed between the suspension plate 63*a* and the outer frame 63*b* so as to make the surface of the protruding portion 63*f* of the suspension plate 63*a* and the surface of the outer frame 63*b* non-coplanar. That is, in this embodiment, the surface of the protruding portion 63*f* is away from the surface of the outer frame 63*b*, and thus is not coplanar with the surface of the outer frame 63*b*. A few amount of filling material (such as the conductive adhesive) is applied on the assembly surface of the outer frame 63*b*, and the piezoelectric actuator 63 is assembled to the resonance sheet 62 by attaching the piezoelectric actuator 63 onto the fixed portion 62*c* of the resonance sheet 62 through hot pressing. By stamping the suspension plate 63*a* of the piezoelectric actuator 63 to form the chamber space 67, the required chamber space 67 can be obtained by adjusting the extension distance of the suspension plate 63*a* of the piezoelectric actuator 63, which effectively simplifies the structural design of the chamber space 67, and also simplifies the manufacturing process and shortens the manufacturing time of the piezoelectric actuator 63. Moreover, the first insulation plate 64, the conductive plate 65, and the second insulation plate 66 are all thin sheets with a frame like structure, and the insulation plate 341, the conductive plate 65, and the second insulation plate 66 are sequentially stacked and assembled on the piezoelectric actuator 63 to form the entire structure of the micro pump as the gas transmission device 6.

Figure 9C:
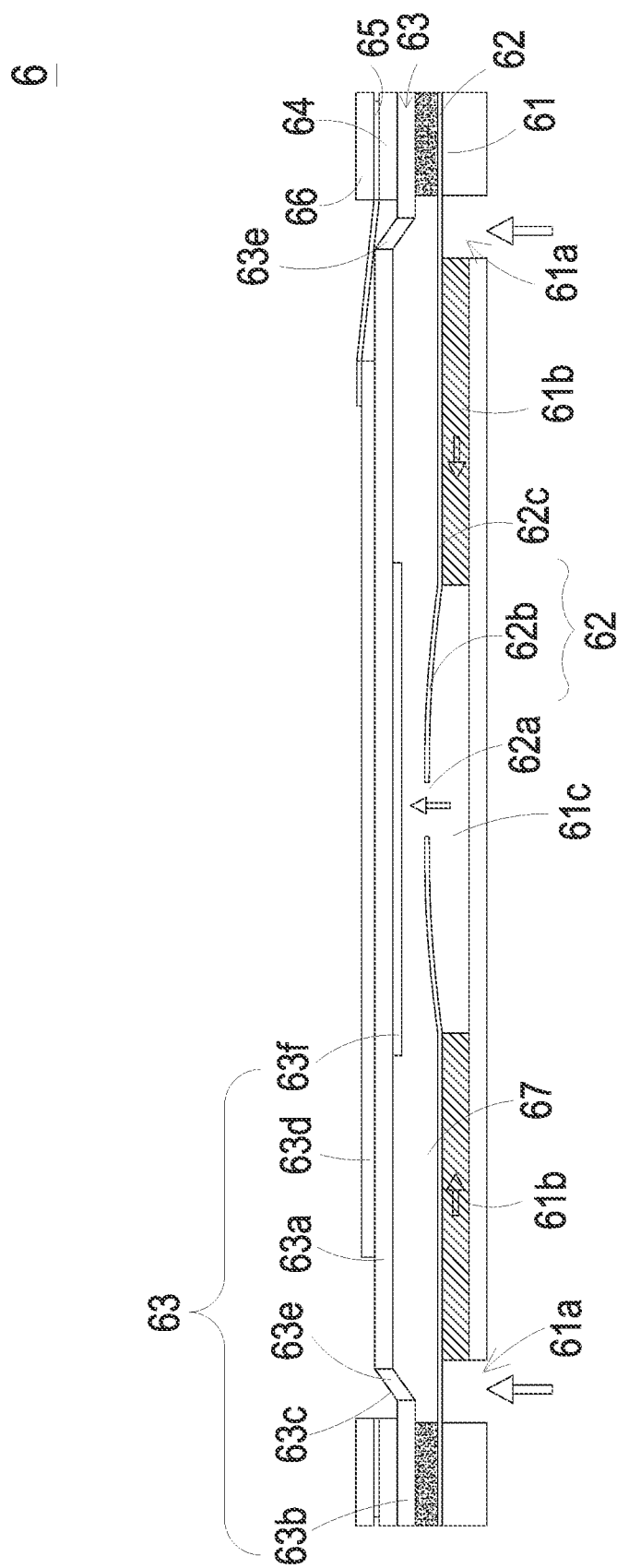
FIG. 9C to FIG. 9E illustrate schematic cross-sectional views showing the micro pump at different operation steps.
Figure 9D:
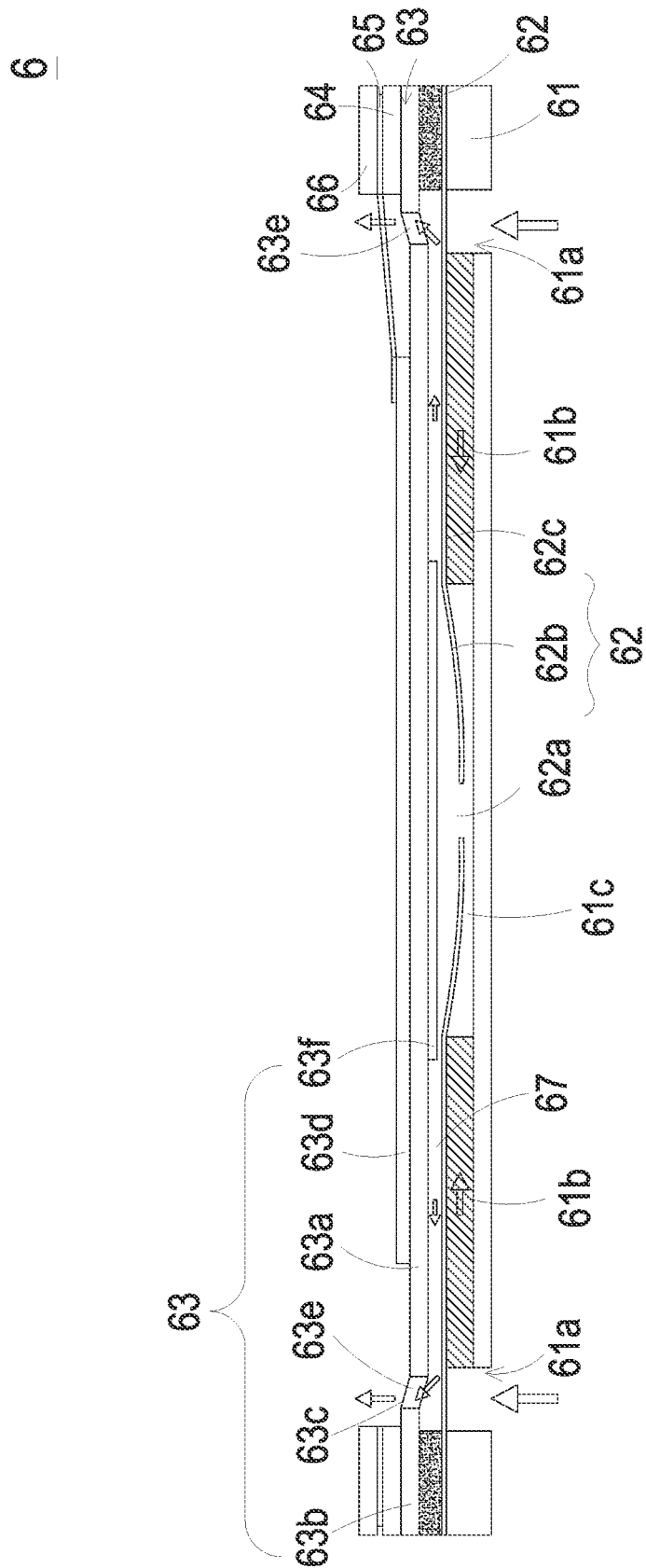
Figure 9E:
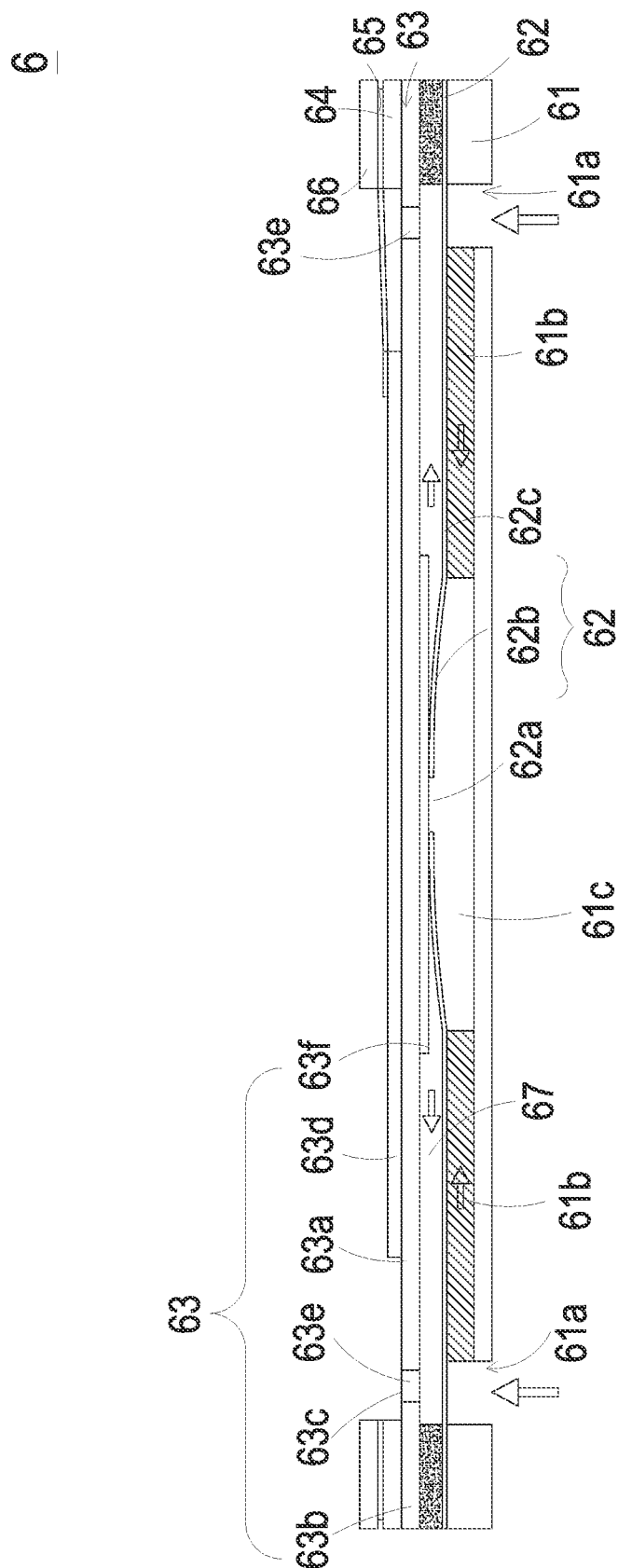

In order to understand the operation of the gas transmission device 6 in gas transmission, please refer to FIG. 9C to FIG. 9E. Please refer to FIG. 9C first, the piezoelectric element 63*d* of the piezoelectric actuator 63 deforms after being applied with a driving voltage, and the piezoelectric element 63*d* drives the suspension plate 63*a* to move away from the resonance sheet 62. Thus, the volume of the chamber space 67 is increased and a negative pressure is generated inside the chamber space 67, thereby drawing the gas in the convergence chamber 61*c* into the chamber space 67. At the same time, owing to the resonance effect, the resonance sheet 62 is moved correspondingly, which also increases the volume of the convergence chamber 61*c*. Furthermore, since the gas inside the convergence chamber 61*c* is drawn into the chamber space 67, the convergence chamber 61*c* is in a negative pressure state as well. Therefore, the gas can be drawn into convergence chamber 61*c* through the inlet hole 61*a* and the convergence channel 61*b*. Then, please refer to FIG. 9D. The piezoelectric element 63*d* drives the suspension plate 63*a* to move toward the resonance sheet 62, thereby compressing the chamber space 67. Similarly, since the resonance sheet 62 resonates with the suspension plate 63*a*, the resonance sheet 62 is moved correspondingly, thereby pushing the gas in the chamber space 67 to be transmitted out of the chamber space 67 through the gap 63*e* so as to achieve gas transmission. Last, please refer to FIG. 9E. When the suspension plate 63*a* is moved resiliently to its original position, and the resonance sheet 62 is also moved away from the inlet plate 61 due to its inertia momentum, the resonance sheet 62 compresses the gas in the chamber space 67 and makes the gas in the chamber space 67 moved toward the at least one gap 63*e* and therefore the volume of the convergence chamber 61*c* is increased. Accordingly, the gas can be drawn into the gas transmission device 6 continuously through the inlet holes 61*a* and the convergence channels 61*b* and converged at the convergence chamber 61*c*. By continuously repeating the operation steps of the gas transmission device 6 shown in FIG. 9C to FIG. 9E, the gas transmission device 6 can make the gas continuously enter into the flow paths formed by the inlet plate 61 and the resonance sheet 62 from the inlet holes 61*a*, thereby generating a pressure gradient and then transmitting the gas outwardly through the gap 63*e*. As a result, the gas can flow at a relatively high speed, thereby achieving the effect of gas transmission.

Moreover, the gas transmission device 6 can be fabricated by microelectromechanical surface micromachining techniques, by which the size of the gas transmission device 6 can be reduced so as to form a microelectromechanical systems (MEMS) micro pump.

To sum up, the present disclosure provides a blood pressure device for measuring pressure the blood pressure in the cardiovascular system of a user. The blood pressure device is made into a wrist wearable type, making it easy to be worn, and thus avoiding the disadvantages of traditional blood pressure devices that are difficult to be carried with. Thus, the blood pressure can be measured anytime and anywhere so as to monitor the user's physical condition. Tightness between the user's skin and the expanders can be adjusted through the expanders, and close-fits against the user's skin during measuring of the blood pressure. When the blood pressure device is not in the measuring mode, the expander would not be inflated and thus makes the blood pressure device of the present invention to be worn more comfortable. Moreover, the blood pressure device can measure the blood pressure value of the user based on the pulse transit time, which can reduce user's stress upon measuring the blood pressure of the user. Thus, the industrial value of the blood pressure device of the present invention is quite high.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A blood pressure device, provided for measuring a blood pressure of a cardiovascular system of a user, the blood pressure device comprising:
a first blood pressure measuring device having a first expander and a first sensor, wherein the first expander is capable of being worn on a first position of a wrist of the user and close-fitting the skin of the user in a non-invasive way, so that the first sensor against the skin of the user to obtain a first blood pressure information of the first position;
a second blood pressure measuring device having a second expander and a second sensor, wherein the second expander is capable of being worn on a second position of the wrist of the user and close-fitting the skin of the user in a non-invasive way, so that the second sensor against the skin of the user to obtain a second blood pressure information of the second position; and
a controller electrically coupled to the first blood pressure measuring device and the second blood pressure measuring device so as to control the first expander to adjust tightness between the first expander and the skin of the user and to control the second expander to adjust tightness between the second expander and the skin of the user, and wherein the controller obtains a pulse transit time from the first blood pressure information and the second blood pressure information, and the controller generates at least one blood pressure value based on the pulse transit time;
wherein the first expander and the second expander respectively comprise an actuator, and wherein the actuator of the first expander controls the first expander to be inflated and expanded, and the actuator of the second expander controls the second expander to be inflated and expanded;
wherein each of the actuators comprise a valve device and at least one gas transmission device, and wherein the at least one gas transmission device is disposed on one side of the valve device;
wherein the gas transmission device is a micro pump, comprising:
an inlet plate having at least one inlet hole, at least one convergence channel, and a convergence chamber, wherein the at least one inlet hole is configured to introduce the gas into the micro pump, and wherein the at least one inlet hole correspondingly penetrates the inlet plate and is in communication with the at least one convergence channel, and the at least one convergence channel is in communication with the convergence chamber, so that the gas introduced by the at least one inlet hole is converged at the convergence chamber;
a resonance sheet attached to the inlet plate, wherein the resonance sheet has a perforation, a movable portion, and a fixed portion, and wherein the perforation is disposed at a center portion of the resonance sheet and corresponds to the convergence chamber of the inlet plate, the movable portion is disposed around a periphery of the perforation and corresponds to the convergence chamber, and the fixed portion is disposed around a periphery of the resonance sheet and is attached to the inlet plate; and
a piezoelectric actuator attached to the resonance sheet, wherein the piezoelectric actuator is correspondingly disposed to the resonance sheet;
wherein a chamber space is formed between the resonance sheet and the piezoelectric actuator, so that when the piezoelectric actuator is driven, the gas is guided into the micro pump through the at least one inlet hole of the inlet plate, is converged at the convergence chamber via the at least one convergence channel, flowed through the perforation of the resonance sheet, and then transmitted owing to a resonance effect between the piezoelectric actuator and the movable portion of the resonance sheet.

2. The blood pressure device according to claim 1, wherein the first sensor is a photoplethysmographic (PPG) sensor or a pulse pressure sensor.

3. The blood pressure device according to claim 1, wherein the second sensor is a photoplethysmographic (PPG) sensor or a pulse pressure sensor.

4. The blood pressure device according to claim 1, wherein the valve device comprises:
a convergence plate having a convergence outlet and a guiding channel in communication with the convergence outlet, wherein a plurality of convergence plate assembly areas is defined on the convergence plate, and each of the convergence plate assembly areas has a convergence trough, a convergence plate convex portion, a discharge trough, and a discharge outlet, wherein the guiding channel communicates with the convergence trough in each of the plurality of convergence plate assembly areas, and the guiding channel is in communication between the convergence trough and the discharge trough in each of the plurality of convergence plate assembly areas, and wherein the convergence plate convex portion protrudes from the discharge trough, and is surrounded by the discharge trough, and wherein the discharge outlet is disposed at a central portion of the convergence plate convex portion;
at least one chamber plate, wherein the convergence plate is disposed on each of the at least one chamber plate, wherein a flow guiding chamber and a receiving trough are disposed in a portion of the at least one chamber plate corresponding to each of the plurality of convergence plate assembly areas of the convergence plate, wherein the flow guiding chamber and the receiving trough are respectively disposed on two opposite surfaces of the at least one chamber plate, and the flow guiding chamber corresponds to the convergence trough of the convergence plate and is in communication with the convergence trough, wherein a confluence chamber is disposed on a bottom of the receiving trough, and at least one communication hole is disposed on a bottom of the confluence chamber to communicate with the flow guiding chamber, and wherein a chamber plate convex portion is disposed in the flow guiding chamber and is surrounded by the at least one communication hole, and wherein a second communication hole is disposed on a portion of the at least one chamber plate corresponding to the discharge trough of each of the plurality of convergence plate assembly areas of the convergence plate, and the second communication hole is in communication with the confluence chamber; and
at least one valve sheet, wherein the at least one valve sheet is between the convergence plate and the at least one chamber plate, and the at least one valve sheet correspondingly abuts against the chamber plate convex portion in the at least one chamber plate, wherein a valve hole is disposed on the at least one valve sheet and corresponds to the chamber plate convex portion, and the valve hole is closed by the chamber plate convex portion, and wherein the at least one valve sheet abuts against the convergence plate convex portion in each of the plurality of convergence plate assembly area of the convergence plate to close the discharge outlet;

wherein the gas transmission device is positioned in the receiving trough of the at least one chamber plate so as to close the confluence chamber and so as to operate to transmit gas into the confluence chamber; and wherein when the gas transmission device operates, the gas transmission device guides the gas into the valve device from the confluence chamber of the at least one chamber plate so as to push the valve sheet to detach from the chamber plate convex portion, whereby the gas passes through the valve hole of the at least one valve sheet and flows into the convergence trough of the convergence plate in communication with the flow guiding chamber, and the gas is converged at the guiding channel and discharged out from the convergence outlet.

5. The blood pressure device according to claim 4, wherein when the gas transmission device is not in operation, the gas at the convergence outlet of the convergence plate is capable of being guided into the convergence trough through the guiding channel, whereby the gas pushes the valve sheet to move, so that the valve hole of the valve sheet abuts against the chamber plate convex portion so as to be closed, and the gas further flows into the discharge trough through the guiding channel to push the valve sheet corresponding to the discharge trough to detach from the convergence plate convex portion, thereby opening the discharge outlet, and the gas is discharged out of the convergence plate from the discharge outlet, thereby achieving a pressure-releasing procedure.

6. The blood pressure device according to claim 1, wherein the piezoelectric actuator comprises:
    a suspension plate in square shape and capable of bending and vibrating;
    an outer frame disposed around a periphery of the suspension plate;
    at least one supporting element connected between the suspension plate and the outer frame to provide a flexible support for the suspension plate; and
    a piezoelectric element having a side length, wherein the side length of the piezoelectric element is smaller than or equal to a side length of the suspension plate, and the piezoelectric element is attached to a surface of the suspension plate so as to drive the suspension plate to bend and vibrate when the piezoelectric element is applied with a voltage.

7. The blood pressure device according to claim 1, wherein the piezoelectric actuator comprises:
    a suspension plate in square shape and capable of bending and vibrating;
    an outer frame disposed around a periphery of the suspension plate;
    at least one supporting element connected between the suspension plate and the outer frame to provide a flexible support for the suspension plate, wherein a surface of the suspension plate and a surface of the outer frame are non-coplanar, so that a chamber space is formed between the surface of the suspension plate and the resonance sheet; and
    a piezoelectric element having a side length, wherein the side length of the piezoelectric element is smaller than or equal to a side length of the suspension plate, and the piezoelectric element is attached to a first surface of the suspension plate so as to drive the suspension plate to bend and vibrate when the piezoelectric element is applied with a voltage.

8. The blood pressure device according to claim 1, wherein the gas transmission device is a microelectromechanical micro pump system.

9. The blood pressure device according to claim 1, wherein the first expander and the second expander are respectively annular belt structures made of elastic material so as to be configured to wrap around the user's wrist or arm, wherein the first expander and the second expander respectively have a gas bag disposed at an inner side of the annular belt structure to form a flat surface, and wherein the gas bag of the first expander is controlled to be inflated and expanded by the actuator of the first expander, and the gas bag of the second expander is controlled to be inflated and expanded by the actuator of the second expander.

10. A blood pressure device, provided for measuring a blood pressure of a cardiovascular system of a user, the blood pressure device comprising:
    a first blood pressure measuring device having a first expander and a first sensor, wherein the first expander is capable of being worn on a first position of a wrist of the user and close-fitting the skin of the user in a non-invasive way, so that the first sensor is configured to close-fit against the skin of the user to obtain a first blood pressure information of the first position;
    a second blood pressure measuring device having a second expander, and a second sensor, wherein the second expander is capable of being worn on a second position of the wrist of the user and close-fitting the skin of the user in a non-invasive way, so that the second sensor is configured to close-fit against the skin of the user to obtain a second blood pressure information of the second position; and
    a controller electrically coupled to the first blood pressure measuring device and the second blood pressure measuring device so as to control the first expander to adjust tightness between the first expander and the skin of the user and to control the second expander to adjust tightness between the second expander and the skin of the user, and wherein the controller obtains a pulse transit time from the first blood pressure information and the second blood pressure information, and the controller generates at least one blood pressure value based on the pulse transit time;
    wherein the first expander and the second expander respectively comprise an actuator, and wherein the actuator of the first expander controls the first expander to be inflated and expanded, and the actuator of the second expander controls the second expander to be inflated and expanded;
    wherein each of the actuators comprise a valve device and at least one gas transmission device, and wherein the at least one gas transmission device is disposed on one side of the valve device;
    wherein the valve device comprises:
    a convergence plate having a convergence outlet and a guiding channel in communication with the convergence outlet, wherein a plurality of convergence plate assembly areas is defined on the convergence plate, and each of the convergence plate assembly areas has a convergence trough, a convergence plate convex portion, a discharge trough, and a discharge outlet, wherein the guiding channel communicates with the convergence trough in each of the plurality of convergence plate assembly areas, and the guiding channel is in communication between the convergence trough and the discharge trough in each of the plurality of convergence plate assembly areas, and wherein the convergence plate convex portion protrudes from the discharge trough, and is surrounded by the discharge trough, and wherein the discharge outlet is disposed at a central portion of the convergence plate convex portion;

at least one chamber plate, wherein the convergence plate is disposed on each of the at least one chamber plate, wherein a flow guiding chamber and a receiving trough are disposed in a portion of the at least one chamber plate corresponding to each of the plurality of convergence plate assembly areas of the convergence plate, wherein the flow guiding chamber and the receiving trough are respectively disposed on two opposite surfaces of the at least one chamber plate, and the flow guiding chamber corresponds to the convergence trough of the convergence plate and is in communication with the convergence trough, wherein a confluence chamber is disposed on a bottom of the receiving trough, and at least one communication hole is disposed on a bottom of the confluence chamber to communicate with the flow guiding chamber, and wherein a chamber plate convex portion is disposed in the flow guiding chamber and is surrounded by the at least one communication hole, and wherein a second communication hole is disposed on a portion of the at least one chamber plate corresponding to the discharge trough of each of the plurality of convergence plate assembly areas of the convergence plate, and the second communication hole is in communication with the confluence chamber; and at least one valve sheet, wherein the at least one valve sheet is between the convergence plate and the at least one chamber plate, and the at least one valve sheet correspondingly abuts against the chamber plate convex portion in the at least one chamber plate, wherein a valve hole is disposed on the at least one valve sheet and corresponds to the chamber plate convex portion, and the valve hole is closed by the chamber plate convex portion, and wherein the at least one valve sheet abuts against the convergence plate convex portion in each of the plurality of convergence plate assembly area of the convergence plate to close the discharge outlet;

wherein the gas transmission device is positioned in the receiving trough of the at least one chamber plate so as to close the confluence chamber and so as to operate to transmit gas into the confluence chamber; and wherein when the gas transmission device operates, the gas transmission device guides the gas into the valve device from the confluence chamber of the at least one chamber plate so as to push the valve sheet to detach from the chamber plate convex portion, whereby the gas passes through the valve hole of the at least one valve sheet and flows into the convergence trough of the convergence plate in communication with the flow guiding chamber, and the gas is converged at the guiding channel and discharged out from the convergence outlet.

11. The blood pressure device according to claim 10, wherein when the gas transmission device is not in operation, the gas at the convergence outlet of the convergence plate is capable of being guided into the convergence trough through the guiding channel, whereby the gas pushes the valve sheet to move, so that the valve hole of the valve sheet abuts against the chamber plate convex portion so as to be closed, and the gas further flows into the discharge trough through the guiding channel to push the valve sheet corresponding to the discharge trough to detach from the convergence plate convex portion, thereby opening the discharge outlet, and the gas is discharged out of the convergence plate from the discharge outlet, thereby achieving a pressure-releasing procedure.

\* \* \* \* \*